(12) United States Patent
Hildbrand et al.

(10) Patent No.: US 8,227,505 B2
(45) Date of Patent: *Jul. 24, 2012

(54) METHOD FOR PREPARING ENANTIOMERICALLY PURE 4-PYRROLIDINO PHENYLBENZYL ETHER DERIVATIVES

(75) Inventors: Stefan Hildbrand, Mumpf (CH); Bruno Lohri, Reinach (CH); Wolfgang Wostl, Grenzach-Wyhlen (DE)

(73) Assignee: Hoffman-La Roche Inc., Nutley, NJ (US)

( * ) Notice: Subject to any disclaimer, the term of this patent is extended or adjusted under 35 U.S.C. 154(b) by 372 days.

This patent is subject to a terminal disclaimer.

(21) Appl. No.: 12/359,356

(22) Filed: Jan. 26, 2009

(65) Prior Publication Data

US 2009/0171100 A1    Jul. 2, 2009

Related U.S. Application Data

(62) Division of application No. 11/370,668, filed on Mar. 8, 2006, now Pat. No. 7,501,528.

(30) Foreign Application Priority Data

Mar. 15, 2005 (EP) .................................... 05102030

(51) Int. Cl.
*A61K 31/4015* (2006.01)
*C07D 207/04* (2006.01)

(52) U.S. Cl. ......... 514/424; 548/541; 548/550; 548/551
(58) Field of Classification Search .................. 548/541, 548/543, 550, 551; 514/424
See application file for complete search history.

(56) References Cited

U.S. PATENT DOCUMENTS

| | | | |
|---|---|---|---|
| 4,526,786 A * | 7/1985 | Bourgery et al. ........... | 514/236.8 |
| 7,037,935 B2 * | 5/2006 | Iding et al. .................... | 514/423 |
| 7,148,362 B2 * | 12/2006 | Iding et al. .................... | 548/531 |
| 7,151,111 B2 * | 12/2006 | Iding et al. .................... | 514/343 |
| 7,235,581 B2 * | 6/2007 | Jolidon et al. ................ | 514/424 |
| 7,456,210 B2 * | 11/2008 | Rodriguez-Sarmiento et al. .............. | 514/424 |
| 7,501,528 B2 * | 3/2009 | Hildbrand et al. ........... | 548/550 |
| 2004/0097578 A1 | 5/2004 | Jolidon et al. | |

FOREIGN PATENT DOCUMENTS

| WO | WO 96/40095 | 12/1996 |
|---|---|---|
| WO | WO 97/33572 | 9/1997 |
| WO | WO 01/34172 | 5/2001 |
| WO | WO 2004/026825 | 4/2004 |
| WO | WO 2004/026826 | 4/2004 |

OTHER PUBLICATIONS

Iding et al (2004): STN International HCAPLUS database, (Columbus, Ohio), Accession No. 2004:267294.*
Ancher et al (1984): STN International HCAPLUS database, (Columbus, Ohio), Accession No. 1984:174812.*
Bach, et al. Proc. Natl. Acad. Sci. USA 85:4934-4938 (1988).
Cesura, et al., A., Prog. Drug Research 38:171-297 (1992).
Fowler, et al. J. Neural. Transm. 49:1-20 (1980).
Benedetti, et al. Biochem. Pharmacol. 38:555-561 (1989).
Saura, et al. Neuroscience 70:755-774 (1996).
Bentué-Ferrer, et al. CNS Drugs 6(3): 217-236 (1996).
Gardner, et al. J. Clin. Psychiatry 57(3):99-104 (1996).
Schlaeger, E. J., & Christensen, K., Cytotechnology 30:71-83 (1999).
Zhou, et al., Analytical Biochemistry 253:169-174 (1997).
Ebbers et al., Tetrahedron: Asymmetry vol. 8, No. 24, pp. 4047-4057 (1997).
Moriarty et al., J. Org. Chem. vol. 58, pp. 2478-2482 (1993).
Jean et al., Tetrahedron Lett., vol. 42, pp. 5645-5649 (2001).
John Wiley & Sons Inc. Comprehensive Organic Transformations (1999) 867-868.
Abstract of Japanese Patent Publications No. Hei 03-95138, Apr. 19, 1991.
Abstract of Japanese Patent Publications No. Sho 53-18529, Feb. 20, 1978.
Japanese Office Action dated Feb. 1, 2011.

* cited by examiner

*Primary Examiner* — Golam M M Shameem
(74) *Attorney, Agent, or Firm* — George W. Johnston; Patricia S. Rocha-Tramaloni; Kimberly J. Prior

(57) ABSTRACT

The invention relates to a method for preparing enantiomerically pure 4-pyrrolidinophenylbenzyl ether derivatives of formula I:

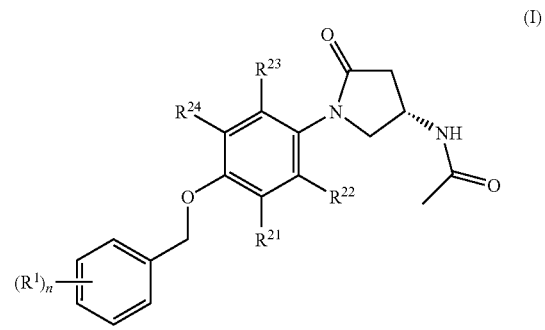

wherein $R^1$, $R^{21}$, $R^{22}$, $R^{23}$, $R^{24}$ and n are as defined in the description and claims and to intermediates useful in the method of the invention as well as salts thereof.

6 Claims, No Drawings

METHOD FOR PREPARING ENANTIOMERICALLY PURE 4-PYRROLIDINO PHENYLBENZYL ETHER DERIVATIVES

PRIORITY TO RELATED APPLICATIONS

This application is a division of U.S. application Ser. No. 11/370,668, filed Mar. 8, 2006, now pending; which claims the benefit of European Application No. 05102030.3, filed Mar. 15, 2005. The entire contents of the above-identified applications are hereby incorporated by reference.

BACKGROUND OF THE INVENTION

Monoamine oxidase (MAO, EC 1.4.3.4) is a flavin-containing enzyme responsible for the oxidative deamination of endogenous monoamine neurotransmitters such as dopamine, serotonin, adrenaline, or noradrenaline, and trace amines, e.g. phenylethyl-amine, as well as a number of amine xenobiotics. The enzyme exists in two forms, MAO-A and MAO-B, encoded by different genes [Bach et al., Proc. Natl. Acad. Sci. USA 85:4934-4938 (1988)] and differing in tissue distribution, structure and substrate specificity. MAO-A has higher affinity for serotonin, octopamine, adrenaline, and noradrenaline; whereas the natural substrates for MAO-B are phenylethylamine and tyramine. Dopamine is thought to be oxidised by both isoforms. MAO-B is widely distributed in several organs including brain [Cesura and Pletscher, Prog. Drug Research 38:171-297 (1992)]. Brain MAO-B activity appears to increase with age. This increase has been attributed to the gliosis associated with aging [Fowler et al., J. Neural. Transm. 49:1-20 (1980)]. Additionally, MAO-B activity is significantly higher in the brains of patients with Alzheimer's disease [Dostert et al., Biochem. Pharmacol. 38:555-561 (1989)] and it has been found to be highly expressed in astrocytes around senile plaques [Saura et al., Neuroscience 70:755-774 (1994)]. In this context, since oxidative deamination of primary monoamines by MAO produces $NH_3$, aldehydes and $H_2O_2$, agents with established or potential toxicity, it is suggested that there is a rationale for the use of selective MAO-B inhibitors for the treatment of dementia and Parkinson's disease. Inhibition of MAO-B causes a reduction in the enzymatic inactivation of dopamine and thus prolongation of the availability of the neurotransmitter in dopaminergic neurons. The degeneration processes associated with age and Alzheimer's and Parkinson's diseases may also be attributed to oxidative stress due to increased MAO activity and consequent increased formation of $H_2O_2$ by MAO-B. Therefore, MAO-B inhibitors may act by both reducing the formation of oxygen radicals and elevating the levels of monoamines in the brain.

Given the implication of MAO-B in the neurological disorders mentioned above, there is considerable interest to obtain potent and selective inhibitors that would permit control over this enzymatic activity. The pharmacology of some known MAO-B inhibitors is for example discussed by Bentue-Ferrer et al. [CNS Drugs 6:217-236 (1996)]. Whereas a major limitation of irreversible and non-selective MAO inhibitor activity is the need to observe dietary precautions due to the risk of inducing a hypertensive crisis when dietary tyramine is ingested, as well as the potential for interactions with other medications [Gardner et al., J. Clin. Psychiatry 57:99-104 (1996)], these adverse events are of less concern with reversible and selective MAO inhibitors, in particular of MAO-B. Thus, there is a need for MAO-B inhibitors with a high selectivity and without the adverse side-effects typical of irreversible MAO inhibitors with low selectivity for the enzyme.

Compounds of Formula (I)

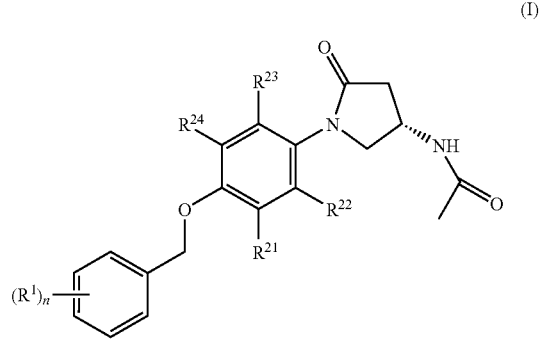

wherein $R^1$ is halogen, halogen —$(C_1$-$C_6)$-alkyl, cyano, $(C_1$-$C_6)$-alkoxy, or halogen —$(C_1$-$C_6)$-alkoxy, $R^{21}$, $R^{22}$, $R^{23}$, and $R^{24}$ are each independently selected from hydrogen and halogen; and n is 0, 1, 2 or 3 are selective monoamine oxidase B inhibitors.

The preparation of MAO-B inhibitors of formula (I) has been disclosed in commonly owned patent application WO 2004/026825. However, that patent application does not disclose the process of the instant invention.

SUMMARY OF THE INVENTION

The invention provides a method for preparing enantiomerically pure 4-pyrrolidinophenylbenzyl ether derivatives. This method produces compounds of formula (I) with high yields and purity. The invention also provides intermediates that are useful in the method of the invention and salts thereof.

More particularly, the present invention provides a method for preparing enantiomerically pure 4-pyrrolidino phenylbenzyl ether derivatives of the formula (I):

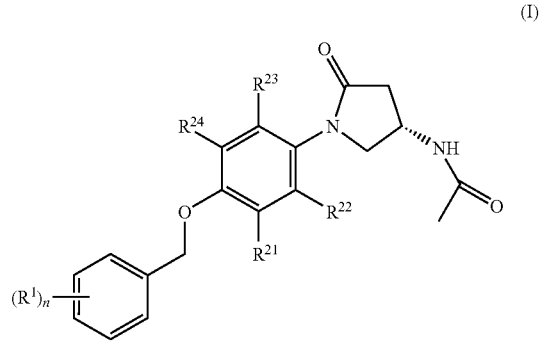

said method comprising a) resolving a racemate of formula (II):

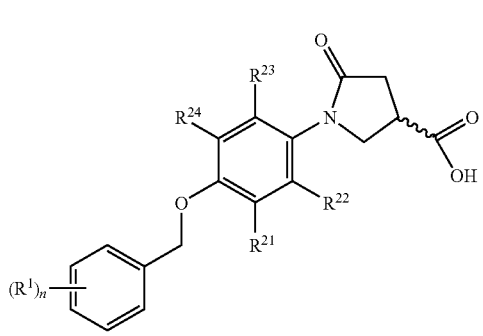

with a resolving agent to obtain the (S)-enantiomer thereof of formula (S)-(II):

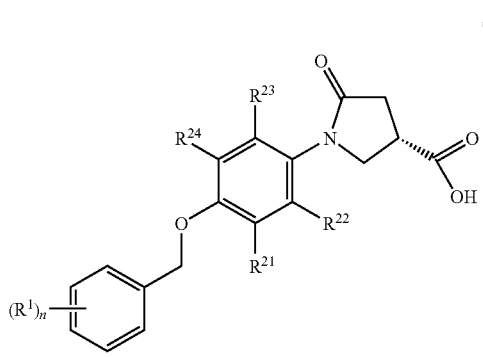

b) converting the enantiomer of formula (S)-(II) into the corresponding primary amide of formula (III):

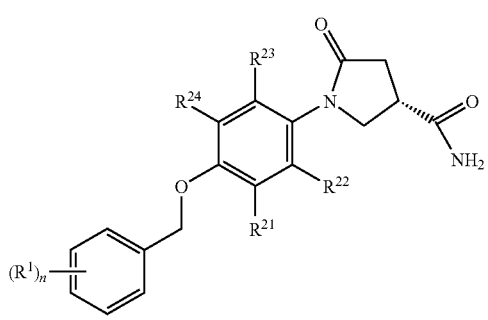

c) either directly reacting the compound of formula (III) with a compound of formula (IV):

in the presence of at least acetic acid and/or acetic anhydride to obtain the compound of formula (I);

d) or reacting the compound of formula (III) with the compound of formula (IV) to obtain a compound of formula (V):

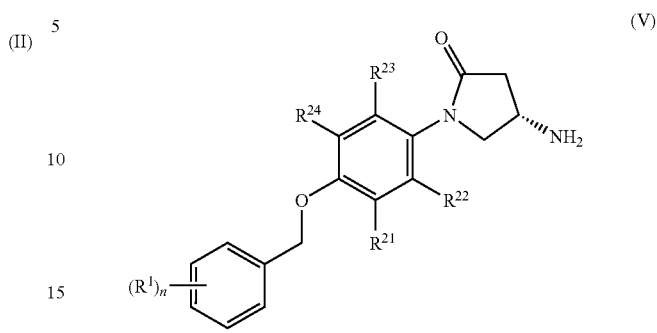

and then reacting the compound of formula (V) with an acetylating agent to obtain the compound of formula (I);
wherein in the above formulae,
Ar is an aryl group, optionally substituted by one or more substituent selected from the group consisting of halogen, nitro, cyano and $(C_1-C_6)$-alkyl;
R is $(C_1-C_6)$-alkyl optionally substituted by one or more halogen atoms;
$R^1$ is halogen, halogen-$(C_1-C_6)$-alkyl, cyano, $(C_1-C_6)$-alkoxy or halogen-$(C_1-C_6)$-alkoxy;
$R^{21}$, $R^{22}$, $R^{23}$ and $R^{24}$ are each independently selected from the group consisting of hydrogen and halogen; and
n is 0, 1, 2 or 3.

DETAILED DESCRIPTION OF THE INVENTION

The following definitions of general terms used herein apply irrespective of whether the terms in question appear alone or in combination. It must be noted that, as used in the specification and the appended claims, the singular forms "a", "an," and "the" include plural forms unless the context clearly dictates otherwise.

In the structural formulae presented herein a wedged bond (⎯▬) denotes that the substituent is above the plane of the paper.

In the structural formulae presented herein a dotted bond (⋯⋯) denotes that the substituent is below the plane of the paper.

The term "lower alkyl or $(C_1-C_6)$-alkyl" used in the present application denotes indifferently straight-chain or branched saturated hydrocarbon residues with 1 to 6 carbon atoms, such as methyl, ethyl, n-propyl, i-propyl, n-butyl, sec-butyl, t-butyl, and the like, preferably with 1 to 3 carbon atoms. Accordingly, the term "$(C_1-C_3)$-alkyl" means a straight-chain or branched saturated hydrocarbon residue with 1 to 3 carbon atoms.

"$(C_1-C_6)$-Alkoxy" means the residue —O—R, wherein R is a $(C_1-C_6)$-alkyl residue as defined herein. Examples of alkoxy radicals include, but are not limited to, methoxy, ethoxy, isopropoxy, and the like.

The term "halogen" denotes fluorine, chlorine, bromine and iodine.

"Halogen-$(C_1-C_6)$-alkyl" or "halogen-$(C_1-C_6)$-alkoxy" means the lower alkyl residue or lower alkoxy residue, respectively, as defined herein substituted in any position with one or more halogen atoms as defined herein. Examples of halogenalkyl residues include, but are not limited to, 1,2-difluoropropyl, 1,2-dichloropropyl, trifluoromethyl, 2,2,2-trifluoroethyl, 2,2,2-trichloroethyl, and 1,1,1-trifluoropropyl, and the like. "Halogenalkoxy" includes trifluoromethyloxy.

"Pharmaceutically acceptable salts" of a compound means salts that are pharmaceutically acceptable, which are generally safe, non-toxic, and neither biologically nor otherwise undesirable, and that possess the desired pharmacological activity of the parent compound. These salts are derived from an inorganic or organic acid or base. If possible, compounds of formula (I) can be converted into pharmaceutically acceptable salts. It should be understood that pharmaceutically acceptable salts are included in the present invention.

The expression "enantiomerically pure" denotes an enantiomeric ratio of the desired enantiomer of at least 95:5, preferably at least 98:2 and still more preferably at least 99.9:0.1 with respect to the undesired enantiomer. The enantiomeric ratio can be determined by HPLC on a chiral column.

More particularly, the present invention provides a method for preparing enantiomerically pure 4-pyrrolidino phenyl-benzyl ether derivatives of the formula (I):

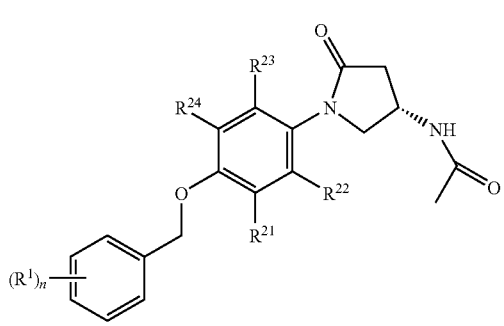
(I)

said method comprising
a) resolving a racemate of formula (II):

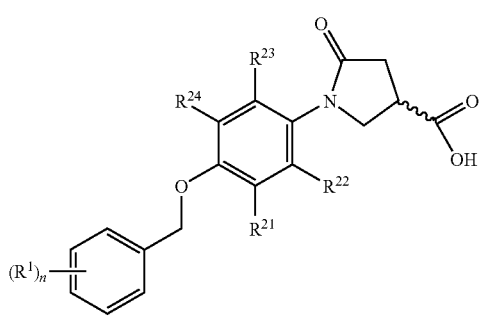
(II)

with a resolving agent to obtain the (S)-enantiomer thereof of formula (S)-(II):

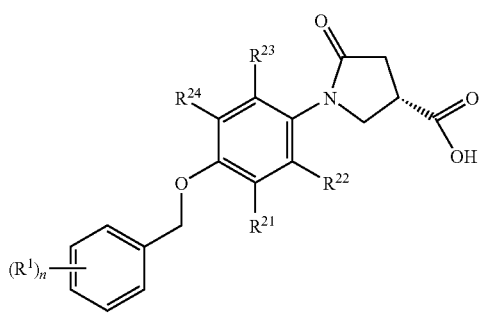
((S)-II)

b) converting the enantiomer of formula (S)-(II) into the corresponding primary amide of formula (III):

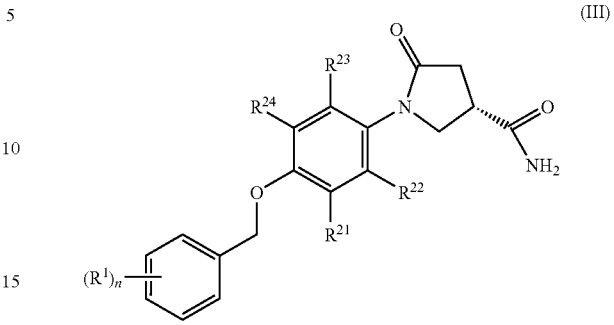
(III)

c) either directly reacting the compound of formula (III) with a compound of formula (IV):

$$ArI(OCOR)_2 \quad (IV)$$

in the presence of at least acetic acid and/or acetic anhydride to obtain the compound of formula (I);

d) or reacting the compound of formula (III) with the compound of formula (IV) to obtain a compound of formula (V):

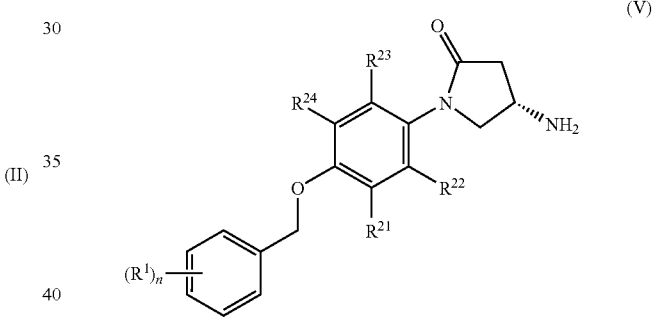
(V)

and then reacting the compound of formula (V) with an acetylating agent to obtain the compound of formula (I);
wherein in the above formulae,
Ar is an aryl group optionally substituted by one or more substituent selected from the group consisting of halogen, nitro, cyano and $(C_1-C_6)$-alkyl;
R is $(C_1-C_6)$-alkyl optionally substituted by one or more halogen atoms;
$R^1$ is halogen, halogen-$(C_1-C_6)$-alkyl, cyano, $(C_1-C_6)$-alkoxy or halogen-$(C_1-C_6)$-alkoxy;
$R^{21}$, $R^{22}$, $R^{23}$ and $R^{24}$ are each independently selected from the group consisting of hydrogen and halogen; and
n is 0, 1, 2 or 3.

It is to be understood that in step a) any suitable resolving agent other than an enzyme can be used. In certain embodiments of the invention the resolving agent used in step a) is selected from the group consisting of (R)-(−)-2-phenylglycinol=(R)-2-amino-2-phenyl-ethanol, (S)-(+)-2-phenylglycinol, cinchonidine, D-phenylalaminol, L-phenylalaminol, (+)-phenylethylamine, (1S,2S)-(+)-thiomicamine, (1S,2S)-(+)-2-amino-1-phenyl-1,3-propanediol, (1S,2R)-(−)-cis-1-amino-2-indanol, L-phenylephrine, (1S,2R)-(+)-N-methylephedrine, L-prolinol, (R)-(−)-2-amino-1-butanol and (R)-(+)-1-(-naphthyl)-ethylamine. The preferred resolving agent is (R)-phenylglycinol.

In particular, the compound of formula (S)-(II) can be obtained by directly preparing a salt of the (S)-(II) compound with a resolving agent capable of forming a salt of the (S)-(II) compound with the racemate (II).

Alternatively, the compound of formula (S)-(II) can be obtained indirectly by preparing a salt of the (R)-(II) compound with a resolving agent capable of forming a salt of the (R)-(II) compound with the racemate (II) and then removing the (R)-(II) compound from the racemate to keep the (S)-(II) compound in the reacting mixture.

Preferred resolving agents capable of forming a salt of the (S)-(II) compound with the racemate (II) are (R)-(−)-2-phenylglycinol, cinchonidine, D-phenylalaminol, (+)-phenylethylamine, (1S,2R)-(−)-cis-1-amino-2-indanol, and L-phenylephrine, the most preferred resolving agent being (R)-(−)-2-phenylglycinol.

Preferred resolving agents capable of forming a salt of the (R)-(II) compound with the racemate (II) are (S)-(+)-2-phenylglycinol, (1S,2S)-(+)-thiomicamine, (1S,2S)-(+)-2-amino-1-phenyl-1,3-propanediol, (1S,2R)-(+)-N-methylephedrine, L-prolinol, (R)-(−)-2-amino-1-butanol and (R)-(+)-1-(-naphthyl)-ethylamine. The preferred resolving agent is (S)-(+)-2-phenylglycinol.

In certain embodiments of the invention, the reaction in step a) is performed without a solvent. In certain other embodiments of the invention a solvent can be used in step a). This solvent can be selected from the group consisting of acetone, isopropanol, acetonitrile, tetrahydrofuran, 2-butanone, isopropanol, EtOH and their mixtures with water. The preferred solvent is a mixture of acetonitrile and water.

In one embodiment, step a) of the method according to invention for resolving a racemate of formula (II) to directly obtain an enantiomer of formula (S)-(II) suitably comprises:

a1) preparing a reaction mixture in a solvent comprising the racemate (II) and a resolving agent capable of forming a salt of the (S)-(II) compound with the racemate (II) to obtain a salt of the compound (S)-(II);

a2) isolating the salt of the compound (S)-(II) from the reaction mixture and liberating said compound (S)-(II) from its salt;

a3) isolating the compound (R)-(II) remaining in the reaction mixture of step a1);

a4) racemizing the isolated compound (R)-(II) to obtain a recycled racemate;

a5) repeating steps a1) to a4) using the recycled racemate in place of the original racemate.

In another embodiment, step a) of the method according to invention for resolving a racemate of formula (II) to indirectly obtain the enantiomer thereof of formula (S)-(II) by removing the (R)-(II) enantiomer suitably comprises:

a1') preparing a reaction mixture in a solvent comprising the racemate (II) and a resolving agent capable of forming a salt of the (R)-(II) compound with the racemate (II) to obtain a salt of the compound (R)-(II);

a2') isolating the salt of the compound (R)-(II) from the reaction mixture and liberating said compound (R)-(II) from its salt;

a3') isolating the compound (S)-(II) remaining in the reaction mixture of step a1');

a4') racemizing the isolated compound (R)-(II) to obtain a recycled racemate;

a5') repeating steps a1') to a4') using the recycled racemate in place of the original racemate.

Steps a2) to a4) and a2') to a4') can be performed using conventional methods and equipment, for example extraction, crystallization, filtration, etc. Steps a1) to a4) and a1') to a4') can be repeated using recycled racemate as many times as necessary to obtain all of the compound (S)-(II) possible from the original reaction mixture.

In certain embodiments of the invention the conversion of the enantiomer of formula (S)-(II) into the corresponding primary amide of formula (III) according to step b) can be performed by using 1,1'-carbonyldiimidazole and a source of ammonia, e.g. aqueous ammonia or ammonium acetate.

In certain other embodiments of the invention the conversion of the enantiomer of formula (S)-(II) into the corresponding primary amide of formula (III) according to step b) can be performed by using N-methylmorpholine, ethyl chloroformate and a source of ammonia, e.g. gaseous ammonia.

Step b) can be performed in the presence or in the absence of a solvent. A solvent can also be used in step b), for example tetrahydrofuran (THF). The resulting compound of formula (III) can then be isolated and purified using conventional methods and equipment such as concentration in vacuo, dilution, extraction, precipitation, filtration, etc.

In Step c) preferred compounds of formula (IV):

$$ArI(OCOR)_2 \qquad (IV)$$

are those compounds wherein Ar is unsubstituted phenyl and R is Me, $CF_3$ or $Cl_3$ or $CCl_3$ for example (diacetoxyiodo)benzene.

Steps c) and d) according to the method of the invention represent alternative routes to obtain the compound of formula (I) starting from the compound of formula (III).

Step c) is a one-step alternative comprising reacting the compound of formula (III) with the compound of formula (IV) in the presence of at least acetic acid and/or acetic anhydride, which directly leads to the compound of formula (I).

In one embodiment of step c), the reaction of the compound of formula (III) with a compound of formula (IV) is performed in the presence of at least acetic acid. In another embodiment of step c), the reaction of the compound of formula (III) with the compound of formula (IV) is performed in the presence of at least acetic anhydride. In still another embodiment of step c), the reaction of the compound of formula (III) with the compound of formula (IV) is performed in the presence of at least acetic acid and acetic anhydride.

The compound of formula (I) can then be isolated and purified using conventional methods and equipment, for example using conventional extraction, filtration, distillation, crystallization, etc.

Step d) is a two-step alternative comprising the reaction of the compound of formula (III) with a compound of formula (IV):

$$ArI(OCOR)_2 \qquad (IV)$$

wherein Ar and R are as defined above,
to obtain a compound of formula (V):

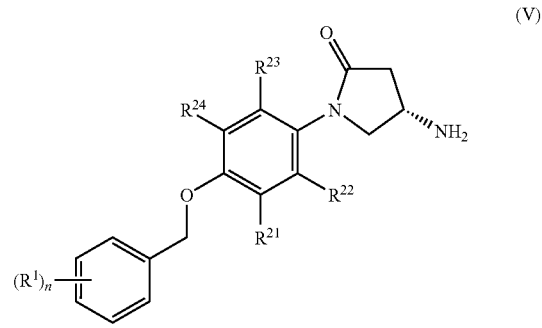

and then reacting the compound of formula (V) with an acetylating agent to obtain the compound of formula (I).

In certain embodiments of step d) according to the invention, the compound of formula (IV) is (diacetoxyiodo)benzene: (PhI(OAc)$_2$).

In certain embodiments of step d) according to the invention, the acetylating agent can be acetic anhydride (Ac$_2$O) or acetyl chloride.

In certain embodiments of the invention step d) can be performed in a suitable solvent, e.g. in tetrahydrofuran (THF) with water, e.g. in a ratio of about 1:1. In certain other embodiments of the invention step d) can be performed in the absence of a solvent.

The compound of formula (I) can then be isolated and purified using conventional methods and equipment.

The racemate of formula (II) can be prepared as described in WO 2004/026825, the content of which is incorporated herein by reference.

The invention hence encompasses the following novel intermediates involved in the method of the invention:

the salts of the compound of formula (S)-(II) with a resolving agent selected from the group consisting of (R)-(−)-2-phenylglycinol, cinchonidine, D-phenylalaminol, (+)-phenylethylamine, (1S,2R)-(−)-cis-1-amino-2-indanol, and L-phenylephrine, the most preferred resolving agent being (R)-(−)-2-phenylglycinol;

and the intermediate of formula (III):

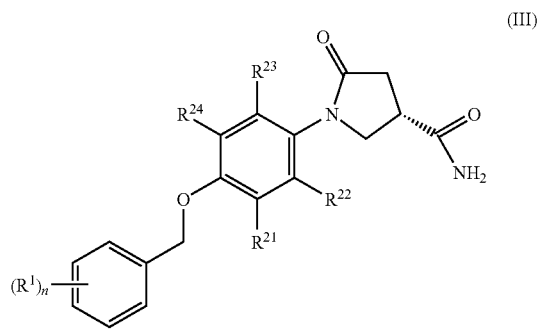

wherein R$^1$, R$^{21}$, R$^{22}$, R$^{23}$, R$^{24}$ and n are as defined hereinabove.

Preferred compound of formula (S)-(II) and salts thereof with the above recited resolving agents are those compounds wherein:
R$^1$ is 3-fluoro;
R$^{21}$, R$^{22}$, R$^{23}$ and R$^{24}$ are hydrogen; and
n is 1.
Preferred intermediate of formula (III) are those compounds wherein:
R$^1$ is 3-fluoro;
R$^{21}$, R$^{22}$, R$^{23}$ and R$^{24}$ are hydrogen; and
n is 1.

In a certain embodiment of the method according to the invention, the racemate (II) is (RS)-1-[4-(3-fluoro-benzyloxy)-phenyl]-5-oxo-pyrrolidine-3-carboxylic acid, (S)-(II) is (S)-1-[4-(3-fluoro-benzyloxy)-phenyl]-5-oxo-pyrrolidine-3-carboxylic acid, the compound of formula (III) is (S)-1-[4-(3-fluoro-benzyloxy)-phenyl]-5-oxo-pyrrolidine-3-carboxylic acid amide using 1,1'-carbonyldiimidazole, the compound of formula (V) is (S)-4-amino-1-[4-(3-fluoro-benzyloxy)-phenyl]-pyrrolidin-2-one, and the compound of formula (I) is (S)—N-{1-[4-(3-fluoro-benzyloxy)-phenyl]-5-oxo-pyrrolidin-3-yl}-acetamide.

The compounds of formula (I) are, as already mentioned hereinabove, monoamine oxidase B inhibitors and can be used for the treatment of diseases in which MAO-B inhibitors might be beneficial. These include acute and chronic neurological disorders, cognitive disorders and memory deficits. Treatable neurological disorders are for instance traumatic or chronic degenerative processes of the nervous system, such as Alzheimer's disease, other types of dementia, minimal cognitive impairment or Parkinson's disease. Other indications include psychiatric diseases such as depression, anxiety, panic attack, social phobia, schizophrenia, eating and metabolic disorders such as obesity, as well as the prevention and treatment of withdrawal syndromes induced by abuse of alcohol, nicotine and other addictive drugs. Other treatable indications may be peripheral neuropathy caused by cancer chemotherapy (WO 97/33,572), reward deficiency syndrome (WO 01/34,172), or the treatment of multiple sclerosis (WO 96/40,095), and other neuroinflammatory diseases.

The compounds of formula (I) are especially useful for the treatment of Alzheimer's disease and senile dementia.

The pharmacological activity of the compounds was tested using the following method: The cDNAs encoding human MAO-A and MAO-B were transiently transfected into EBNA cells using the procedure described by Schlaeger and Christensen [Cytotechnology 15:1-13 (1998)]. After transfection, cells were homogenised by means of a Polytron homogenizer in 20 mM Tris HCl buffer, pH 8.0, containing 0.5 mM EGTA and 0.5 mM phenylmethanesulfonyl fluoride. Cell membranes were obtained by centrifugation at 45,000×g and, after two rinsing steps with 20 mM Tris HCl buffer, pH 8.0, containing 0.5 mM EGTA, membranes were eventually re-suspended in the above buffer and aliquots stored at −80° C. until use.

MAO-A and MAO-B enzymatic activity was assayed in 96-well-plates using a spectrophotometric assay adapted from the method described by Zhou and Panchuk-Voloshina [Analytical Biochemistry 253:169-174 (1997)]. Briefly, membrane aliquots were incubated in 0.1 M potassium phosphate buffer, pH 7.4, for 30 min at 37° C. containing different concentrations of the compounds. After this period, the enzymatic reaction was started by the addition of the MAO substrate tyramine together with 1 U/ml horse-radish peroxidase (Roche Biochemicals) and 80 μM N-acetyl-3,7-dihydroxyphenoxazine (Amplex Red, Molecular Probes). The samples were further incubated for 30 min at 37° C. in a final volume of 200 μl and absorbance was then determined at a wavelength of 570 nm using a SpectraMax plate reader (Molecular Devices). Background (non-specific) absorbance was determined in the presence of 10 μM clorgyline for MAO-A or 10 μM L-deprenyl for MAO-B. IC$_{50}$ values were determined from inhibition curves obtained, using nine inhibitor concentrations in duplicate, by fitting data to a four parameter logistic equation using a computer program.

The compounds of the present invention are specific MAO-B inhibitors. The IC$_{50}$ values of preferred compounds of formula (I) as measured in the assay described above are in the range of 1 μM or less, typically 0.1 μM or less, and ideally 0.02 μM or less.

The present invention also provides pharmaceutical compositions containing compounds of the invention and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compound of the invention, contain a pharmaceutically acceptable carrier. Suitable pharmaceutically acceptable carriers include pharmaceutically inert inorganic or organic carriers. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula I, but as a rule are not necessary.

Suitable carriers for suppositories are, for example, natural or hardened oils, waxes, fats, semi-liquid or liquid polyols and the like.

In addition, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They may also contain other therapeutically valuable substances.

Compounds of the present invention can be formulated into such pharmaceutical compositions, for example, by bringing one or more compounds of the invention, and if desired, one or more other therapeutically valuable substance into a galenical dosage form together with one or more therapeutically inert carrier.

The dosage at which compounds of the invention can be administered can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

The following examples are provided for illustration of the invention. They should not be considered as limiting the scope of the invention, but merely as being representative thereof. The abbreviation "RT" means "room temperature".

Example 1

Preparation of rac-1-[4-(3-fluoro-benzyloxy)-phenyl]-5-oxo-pyrrolidine-3-carboxylic Acid (Compound of Formula (II))

4-(3-Fluoro-benzyloxy)-phenylamine (31.2 g, 144 mmol) was dissolved in toluene (208 mL) and acetic acid (52 mL). Itaconic acid (18.96 g, 144 mmol) was added to the stirred mixture. The mixture was heated to reflux (101° C.) and kept at this temperature for 3 h. On cooling, the product started to crystallize. At 10° C., heptane (125 mL) was added to the suspension which was stirred 1 h at 0° C. and filtered. The crystals were washed with toluene/heptane 1:1 and with heptane and dried in vacuo to afford the crude product (43.2 g). The crude product was purified by treatment with hot isopropyl acetate to give rac-1-[4-(3-fluoro-benzyloxy)-phenyl]-5-oxo-pyrrolidine-3-carboxylic acid (40.5 g, 86%; HPLC: 99.2% area), m.p. 148-149° C. (uncorr.).

Example 2

Preparation of (S)-1-[4-(3-fluoro-benzyloxy)-phenyl]-5-oxo-pyrrolidine-3-carboxylic Acid [(S)-(II)] Including Recovery of the Undesired Enriched (R)-(II) and its Racemization (Step a) According to the Invention)

a) Preparation of the Salt of the Compound of Formula (S)-(II) with (R)-(−)-2-phenylglycinol rac-1-[4-(3-Fluoro-benzyloxy)-phenyl]-5-oxo-pyrrolidine-3-carboxylic acid (15.0 g, 45.6 mmol) was dissolved in acetonitrile/water 95:5 (150 mL) at 75° C. At this temperature, a solution of (R)-(−)-2-phenylglycinol (6.25 g, 45.6 mmol) in acetonitrile/water 95:5 (10 mL) was added. The current for the heating bath was turned off and crystallization was initiated by addition of some seeding crystals. Stirring was continued for 3 h while the suspension slowly cooled to room temperature. The crystals were collected by filtration, washed with warm (40° C.) acetonitrile and dried in vacuo to afford the title salt (9.9 g, 47%) in >99.9:0.1 dr as determined by HPLC, $[\alpha]_D$ −4.7 (c=1, MeOH).

b) Liberation of the Compound of Formula (S)-(II) from the Salt

In a separation funnel, the main portion of the above salt (8.95 g, 19.2 mmol) was added to ethyl acetate (140 mL). Under occasional shaking, ice water (~100 mL) and 2 N sulfuric acid (~25 mL) was added in several portions until pH 2 was reached. The aqueous phase was separated and extracted with ethyl acetate (140 mL). The organic layers were washed with diluted brine, combined, dried over sodium sulfate and concentrated to a volume of ~40 mL. Heptane (30 mL) was added to the suspension which was stirred 2 h at 0° C. The crystals were collected by filtration, washed with heptane and dried in vacuo. Purification of the product by treatment with hot isopropyl acetate afforded the (S)-1-[4-(3-fluoro-benzyloxy)-phenyl]-5-oxo-pyrrolidine-3-carboxylic acid (6.37 g, 47% based on racemic acid) as white crystals, m.p. 157° C. According to HPLC determination, the purity was 100% (area) and the enantiomeric ratio>99.9:0.1.

c) Isolation of the Enriched (R)-(II) Compound

The mother liquor obtained from the isolation of the phenylglycinol salt of the (S)-(II) compound as described in section a) was concentrated to give a crude phenylglycinol salt (11.4 g) containing the enriched (R)-(II) compound. Together with ethyl acetate (140 mL) this material was added to the acidic aqueous phase remaining from the liberation of the (S)-(II) compound described in section b). The aqueous phase resulting after dissolution of the salt was still acidic. After thorough mixing the aqueous phase was separated and extracted with another portion of ethyl acetate (140 mL). The organic phases were washed with half-concentrated aqueous sodium chloride, combined, dried over sodium sulfate (75 g) and concentrated to a volume of ~40 mL. Heptane (30 mL) was added to the suspension which was stirred 2 h at 0° C. The crystals were collected by filtration, washed with heptane and dried in vacuo to afford enriched (R)-1-[4-(3-fluoro-benzyloxy)-phenyl]-5-oxo-pyrrolidine-3-carboxylic acid (7.4 g, 49% based on racemic acid) as a white solid. The purity of the material by HPLC was 98.8% (area) and the enantiomeric ratio (R):(S) was determined as 91.5:8.5.

d) One-Pot Racemization of the Enriched (R)-(II) Compound

The enriched (R)-(II) compound (7.4 g) obtained as described in section c) was suspended in methanol (50 mL). To the suspension conc. sulfuric acid (0.11 g) and 2,2-dimethoxypropane was added. The mixture was stirred 2 h at 80° C., until the enriched (R)-(II) compound was completely converted to the methyl ester as monitored by HPLC. After cooling to 5° C., a solution of 5.4 M sodium methoxide in methanol (2.91 mL) diluted with methanol (4 mL) was added dropwise within 10 min. The resulting reaction mixture was stirred 20 h at room temperature and then cooled to 10° C. At this temperature, 2 N NaOH (40 mL) was added dropwise over 20 min. The reaction mixture was stirred at room temperature for 2 h and then concentrated in vacuo until the methanol was removed. At 10° C., ice (25 g) was added to the residue followed by dropwise addition of 2 N sulfuric acid until pH 2 was reached. The resulting suspension was stirred for an additional hour. The product was collected by filtration, washed with water until neutral and dried in vacuo at 40° C. to afford rac-1-[4-(3-fluoro-benzyloxy)-phenyl]-5-oxo-pyrrolidine-3-carboxylic acid (7.1 g) as white powder. According to HPLC determination, the purity was 97.3% (area) and the enantiomeric ratio 51.5:48.5.

Example 3

Resolution Using 0.7 eq (R)-Phenylglycinol (step a) According to the Invention)

The salt of the (S)-(II) compound with (R)-(−)-2-phenylglycinol was prepared in an analogous manner as described in Example 2 a) from rac-1-[4-(3-fluoro-benzyloxy)-phenyl]-5-oxo-pyrrolidine-3-carboxylic acid (5 g, 15.2 mmol) in acetonitrile/water 95:5 (50 mL) using a solution of only 1.46 g (R)-(−)-2-phenylglycinol (10.6 mmol, 0.7 eq) in acetonitrile/water 95:5 (3.3 mL). From the salt (3.2 g, 45% based on racemic acid) obtained in 99.7:0.3 diastereomeric ratio the (S)-(II) compound was liberated and purified in a similar manner as described in Example 2b) to afford (S)-1-[4-(3-fluoro-benzyloxy)-phenyl]-5-oxo-pyrrolidine-3-carboxylic acid (2.21 g, 44% based on racemic acid) in high purity (HPLC: 99.4% area) and with >99.9:0.1% er.

Example 4

Resolution Using 0.6 eq (R)-Phenylglycinol (Step a) According to the Invention)

a) Preparation of the Salt of the (S)-(II) Compound with (R)-(−)-2-Phenylglycinol The salt of the (S)-(II) compound with (R)-(−)-2-phenylglycinol was prepared in an analogous manner as described in Example 2 a) from rac-1-[4-(3-fluoro-benzyloxy)-phenyl]-5-oxo-pyrrolidine-3-carboxylic acid (60.00 g, 0.182 mol) in a mixture of acetonitrile (560 mL) and water (34 mL) using a solution of only 15.00 g (R)-(−)-2-phenylglycinol (0.109 mol, 0.6 eq) in a mixture of acetonitrile (72 mL) and water (6 mL) to yield 34.49 g (40% based on racemic acid) of the salt (dr 99.7:0.3).

b) Liberation of the (S)-(II) Compound from the Salt

A suspension of the above salt (33.00 g, 70.74 mmol) in water (495 mL) was treated at 20-25° C. with 55.2 g sulfuric acid (10%) and the resulting suspension (pH 1.4-1.7) was stirred at 20-25° C. for 2-3 h. The crystals were collected by filtration, washed with water (2×125 mL) and dried in vacuo to afford (S)-1-[4-(3-fluoro-benzyloxy)-phenyl]-5-oxo-pyrrolidine-3-carboxylic acid (22.94 g, 40% based on racemic acid) as white crystals. According to HPLC determination, the purity was 99.9% (m/m) and the enantiomeric ratio 99.7:0.3.

Example 5

Salt Formation Using 0.5 eq (R)-(−)-2-phenylglycinol (Step a) According to the Invention)

The salt of the (S)-(II) compound with (R)-(−)-2-phenylglycinol was prepared in an analogous manner as described in Example 2 a) from rac-1-[4-(3-fluoro-benzyloxy)-phenyl]-5-oxo-pyrrolidine-3-carboxylic acid (10 g, 30.4 mmol) in acetonitrile/water 95:5 (100 mL) using a solution of only 2.083 g (R)-(−)-2-phenylglycinol (15.2 mmol, 0.5 eq) in acetonitrile/water 95:5 (6.7 mL). The salt (5.6 g, 39.5% based on racemic acid) was obtained in 99.8:0.2 diastereomeric ratio.

Example 6

Resolution in Isopropanol/Water (Step a) According to the Invention)

a) Preparation of the Salt of the (S)-(II) Compound with (R)-(−)-2-Phenylglycinol rac-1-[4-(3-Fluoro-benzyloxy)-phenyl]-5-oxo-pyrrolidine-3-carboxylic acid (5.0 g, 15.2 mmol) was dissolved in a mixture of isopropanol (47.5 mL) and water (2.5 mL) at 75° C. At this temperature, (R)-(−)-2-phenylglycinol (2.08 g, 15.2 mmol) was added. The electrical power for the heating bath was turned off and crystallization was initiated by addition of some seeding crystals. After 30 minutes the heating bath was removed and stirring was continued while the suspension slowly cooled to room temperature. After 4 h, the crystals were collected by filtration, washed with 95% aq. isopropanol and dried in vacuo to afford crude salt (3.48 g) in 96.5:3.5 dr as determined by HPLC. The crude salt was treated in hot 95% aq. isopropanol to yield, after isolation, the title salt (3.24 g, 46%) in 97.9:2.1 dr.

b) Liberation of the (S)-(II) Compound from the Salt

The above salt (3.24 g, 6.94 mmol) was treated with ethyl acetate (50 mL), ice (10 g) and 2 N sulfuric acid (4 mL). The aqueous phase was separated and extracted with ethyl acetate (20 mL). The organic layers were washed with diluted brine, combined, dried over sodium sulfate (5 g) and concentrated. The residue (2.21 g) was treated 20 h in refluxing isopropyl acetate (8 mL). After cooling, the crystals were collected by filtration, washed with isopropyl acetate (2×3 mL) and dried in vacuo to afford (S)-1-[4-(3-fluoro-benzyloxy)-phenyl]-5-oxo-pyrrolidine-3-carboxylic acid (2.02 g, 40% based on racemic acid) in >99.9:0.1 er.

Examples 7-23

Resolution Experiments Using Alternative Resolving Agents (Comparative Examples) (Step a) According to the Invention)

Under stirring rac-1-[4-(3-fluoro-benzyloxy)-phenyl]-5-oxo-pyrrolidine-3-carboxylic acid (100 mg) was dissolved in 95% aq. EtOH (1 mL) at 50° C. The resolving agent (1 eq) was added and the resulting mixture was slowly cooled to room temperature. Stirring was continued overnight. The crystals formed were isolated by filtration. In cases where no crystals appeared, diisopropyl ether (0.2 mL) was added and stirring was continued for some time before isolation of the crystals. From the crystalline salt the free acid was isolated by extraction with ethyl acetate after acidification using dilute sulfuric acid. The enantiomeric ratio (S):(R) was determined by HPLC on a chiral column and the results are shown in Table 1.

TABLE 1

| Resolving agent | Yield (%) of free acid | (S):(R) | Remarks |
| --- | --- | --- | --- |
| (S)-(+)-2-Phenylglycinol | 34 | 17:83 | |
| Cinchonidine | 65 | 72:28 | |
| D-Phenylalaninol | 36 | 69:31 | |
| (R)-(+)-1-Phenylethylamine | 28 | 68:32 | |
| (1S,2S)-(+)-Thiomicamine | 40 | 33:67 | |
| (1S,2S)-(+)-2-Amino-1-phenyl-1,3-propanediol | 62 | 34:66 | |

TABLE 1-continued

| Resolving agent | Yield (%) of free acid | (S):(R) | Remarks |
| --- | --- | --- | --- |
| Quinine | | | No crystals formed |
| (−)-Sparteine | | | No crystals formed |

Examples 24-33

Resolution Experiments in Various Solvents (Including Comparative Examples) (Step a) According to the Invention)

Under stirring rac-1-[4-(3-fluoro-benzyloxy)-phenyl]-5-oxo-pyrrolidine-3-carboxylic acid was dissolved in hot solvent. The resolving agent (1 eq) was added and the resulting mixture was slowly cooled to room temperature. Stirring was continued overnight. The crystals formed were isolated by filtration. From a sample of the crystalline salt the free acid was isolated by extraction with ethyl acetate after acidification using dilute sulfuric acid. The enantiomeric ratio (S):(R) was determined by HPLC on a chiral column. The results are shown in Table 2.

TABLE 2

Results in various solvents (10 mL/1 g rac-acid)

| Resolving agent (eq) | Amt. of rac-acid (g) | Solvent | Yield of salt (%) | Enantiomeric ratio (S):(R) |
| --- | --- | --- | --- | --- |
| (R)-(−)-2-Phenylglycinol (1.0) | 1.0 | 95% aq. acetone | 50 | 93:7 |
| (R)-(−)-2-Phenylglycinol (1.0) | 5.0 | 95% aq. isopropanol | 49 | 97:3 |
| (R)-(−)-2-Phenylglycinol (1.0) | 1.0 | 95% aq. acetonitrile | 39 | 99.1:0.9 |
| (R)-(−)-2-Phenylglycinol (1.0) | 1.0 | 95% aq. THF | 27 | 95:5 |
| (R)-(−)-2-Phenylglycinol (0.55) | 1.0 | 95% aq. 2-butanone | 32 | 99.7:0.3 |
| Cinchonidine (1.0) | 0.5 | 95% aq. isopropanol | 88 | 55:45 |
| D-Phenylalaninol (1.0) | 0.5 | 95% aq. isopropanol | 66 | 54:46 |
| (1S,2S)-(+)-2-Amino-1-phenyl-1,3-propanediol (1.0) | 0.5 | 95% aq. isopropanol | 80 | 45:55 |
| (1S,2R)-(−)-cis-1-Amino-2-indanol (1.0) | 0.2 | 95% aq. EtOH | 60 | 54:46 |
| (R)-(+)-1-(-Naphthyl)-ethylamine (1.0) | 0.5 | 95% aq. acetonitrile | 74 | 46:54 |

TABLE 1-continued

| Resolving agent | Yield (%) of free acid | (S):(R) | Remarks |
| --- | --- | --- | --- |
| L-Phenylephrine | 62 | 61:39 | |
| L-Prolinol | 44 | 43:57 | |
| (R)-(−)-2-Amino-1-butanol | 30 | 45:55 | |
| (1S,2R)-(+)-N-Methyl-ephedrine | 27 | 47:53 | |
| (+)-Dehydroabietylamine | 10 | 48:52 | |
| Brucine | | | No crystals formed |
| Cinchonine | | | No crystals formed |
| D-(+)-Norephedrine | | | No crystals formed |
| Quinidine | | | No crystals formed |

Example 34

Preparation of (S)-1-[4-(3-fluoro-benzyloxy)-phenyl]-5-oxo-pyrrolidine-3-carboxylic Acid Amide Using 1,1'-carbonyldiimidazole (Compound of Formula (III)) (Step b) According to the Invention)

1,1'-carbonyldiimidazole (8.27 g, 51.0 mmol) was suspended and partly dissolved in tetrahydrofuran (110 mL) at 18° C. (S)-1-[4-(3-fluoro-benzyloxy)-phenyl]-5-oxo-pyrrolidine-3-carboxylic acid (14.0 g, 42.5 mmol; enantiomeric purity (S):(R)=99.5:0.5) was added as a solid together with tetrahydrofuran (30 mL) used for rinsing. The turbid solution, which turned into a white suspension after 15 min, was stirred 1 h at 16-20° C. and then transferred into a stirred 25% aqueous ammonia solution (7.95 mL) in tetrahydrofuran (80 mL). The last part of the white suspension was transferred with the aid of tetrahydrofuran (10 mL) for rinsing. After stirring for 0.5 h the reaction mixture was concentrated in vacuo to a volume of ~70 mL and diluted with water (300 mL). Some ice was added to keep the temperature at 20-25° C. The white precipitate was collected by filtration, washed with water/tetrahydrofuran 80:20 and with heptane. Drying in vacuo at 20-45° C. afforded (S)-1-[4-(3-fluoro-benzyloxy)-phenyl]-5-oxo-pyrrolidine-3-carboxylic acid amide (13.5 g, 96%) as a white solid. The purity of the material by HPLC was 96.9% (area) and the enantiomeric ratio (S):(R) was determined as 99.7:0.3.

Example 35

Alternative Method for the Preparation of (S)-1-[4-(3-fluoro-benzyloxy)-phenyl]-5-oxo-pyrrolidine-3-carboxylic Acid Amide (Compound of Formula (III)) (Step b) According to the Invention)

To (S)-1-[4-(3-fluoro-benzyloxy)-phenyl]-5-oxo-pyrrolidine-3-carboxylic acid (2.0 g, 6.07 mmol; enantiomeric purity (S):(R)>99.9:0.1) in tetrahydrofuran (40 mL), N-methylmorpholine (676 mg, 6.68 mmol) was added at 0° C. After stirring for 20 min, a solution of ethyl chloroformate (725 mg, 6.68 mmol) was added dropwise over 10 min, and stirring at 0° C. was continued for another 20 min. Ammonia (excess) was then bubbled for 15 min through the resulting suspension. The reaction mixture was warmed up to room temperature and stirred for 15 min. Water (50 mL) was added, and the tetrahydrofuran was evaporated in vacuo. The product, which precipitated, was collected by filtration, washed with water and tert-butyl methyl ether and dried at 45° C. in vacuo to afford (S)-1-[4-(3-fluoro-benzyloxy)-phenyl]-5-oxo-pyrrolidine-3-carboxylic acid amide (1.75 g, 88%). The purity of the product by HPLC was 98.9% (area) and the enantiomeric ratio (S):(R) was determined as 99.8:0.2.

Example 36

Preparation of (S)-4-amino-1-[4-(3-fluoro-benzyloxy)-phenyl]-pyrrolidin-2-one (Compound of Formula (V)) (Step d) According to the Invention)

(S)-1-[4-(3-Fluoro-benzyloxy)-phenyl]-5-oxo-pyrrolidine-3-carboxylic acid amide (10.0 g, 30.5 mmol; enantiomeric purity (S):(R)=99.6:0.4, prepared using the method described in example 34) was suspended in a mixture of tetrahydrofuran (80 mL) and water (80 mL). Under stirring (diacetoxyiodo)benzene (12.75 g, 39.6 mmol) was added in one portion at 20° C. Stirring was continued and a water bath was used to keep the temperature at 20° C. After a total reaction time of 3.5 h, less than 0.5% starting material was left according to HPLC. To the reaction mixture ethyl acetate (100 mL) and aqueous 1 N methanesulfonic acid (50 mL) were added. Tetrahydrofuran and ethyl acetate were removed by evaporation in vacuo and another portion of ethyl acetate (100 mL) was added to the residual mixture. The urea type by-product was removed by filtration and washed with some ethyl acetate and water. The filtrate was transferred into a separatory funnel. The aqueous phase was separated and extracted with ethyl acetate. Each of the organic phases were washed with aqueous 0.1 N methanesulfonic acid (2×40 mL). The aqueous phases were combined and the dissolved ethyl acetate was removed in vacuo. At 0° C. the pH was adjusted to 11 by addition of cold 40% aqueous NaOH and ice. The precipitate was collected by filtration, washed with water until the filtrate was neutral and dried in vacuo to afford (S)-4-amino-1-[4-(3-fluoro-benzyloxy)-phenyl]-pyrrolidin-2-one (7.0 g, 76%), chemical purity as determined by HPLC (area): 98.8%. The product was used for the following step without further purification.

Example 37

Preparation of (S)—N-{1-[4-(3-fluoro-benzyloxy)-phenyl]-5-oxo-pyrrolidin-3-yl}-acetamide (Compound of Formula (I)) (Step d) According to the Invention)

In the reaction flask, (S)-4-amino-1-[4-(3-fluoro-benzyloxy)-phenyl]-pyrrolidin-2-one (7.0 g, 23.3 mmol), prepared as described in the previous example, was charged together with dichloromethane (70 mL). At 40° C., a solution of acetic anhydride (2.97 g, 29.1 mmol) in dichloromethane (10 mL) was added dropwise under stirring over 30 min. After a reaction time of 1.5 h, no starting material was left according to HPLC. Acetone (250 mL) was added and the mixture was concentrated in vacuo to a volume of ~50 mL. The residue was dissolved in acetone (250 mL) at 60° C. The warm solution was treated with charcoal, the resulting suspension filtered and the charcoal washed with warm acetone. The filtrate was concentrated at 60° C. to a volume of ~50 mL when the product started to crystallize. At room temperature, tert-butyl methyl ether (100 mL) was added and the suspension was kept at this temperature overnight. The crystals were collected by filtration, washed with tert-butyl methyl ether and dried in vacuo to afford (S)—N-{1-[4-(3-fluoro-benzyloxy)-phenyl]-5-oxo-pyrrolidin-3-yl}-acetamide (7.0 g, 88%) as an off-white powder. The purity of the material by HPLC was 99.4% (area) and the enantiomeric ratio (S):(R) was determined as >99.9:0.1. The result of the elemental analyses (C,H,N,F,O) corresponded to the expected values.

Example 38

Preparation of (S)—N-{1-[4-(3-fluoro-benzyloxy)-phenyl]-5-oxo-pyrrolidin-3-yl}-acetamide (Compound of Formula (I)) (Step c) According to the Invention)

To a solution of (S)-1-[4-(3-fluoro-benzyloxy)-phenyl]-5-oxo-pyrrolidine-3-carboxylic acid amide (20.00 g, 60.91 mmol), (diacetoxyiodo)benzene (25.60 g, 79.48 mmol) und sodium acetate (10.00 g, 12.19 mmol) in acetic acid (190 mL) was added acetic anhydride (20 mL) and the clear solution was heated to 60° C. and stirred at this temperature for 16-20 h. The mixture was cooled to room temperature and 10% aqueous sodium sulfite solution (30 mL) was added dropwise. Water (200 mL) was then added and the resulting suspension was concentrated at 50-60° C. and 150-100 mbar. Another portion of water (200 mL) was added and the suspension was concentrated. This was repeated a third time with 100 mL water. To the suspension was then added water (300 mL) and dichloromethane (400 mL) and the layers were separated. The aqueous phase was extracted with dichloromethane (200 mL). The combined organic layers were washed with water (3×200 mL). Dichloromethane was then distilled off and continuously replaced by ethanol (500 mL) to a final volume of about 300 mL. This mixture was then heated to reflux temperature and the clear solution was treated with carbon (1.4 g). The black mixture was filtered and from the filtrate the ethanol was distilled off and replaced by 2-butanone (260 mL). The mixture was heated to 75-79° C. and stirred at this temperature for 1 h. Upon cooling and seeding the product started to crystallize at 60° C. The mixture was cooled to 0-5° within 2-3 h and stirred at this temperature for 1-2 h. The crystals were collected by filtration, washed with 2-butanone (80 mL) and dried in vacuo to afford 15.79 g (75%) of the title compound as white crystals. According to HPLC determination, the purity was 99.0% (m/m) and the enantiomeric ratio 99.9:0.1.

The invention claimed is:

1. A compound of formula (III):

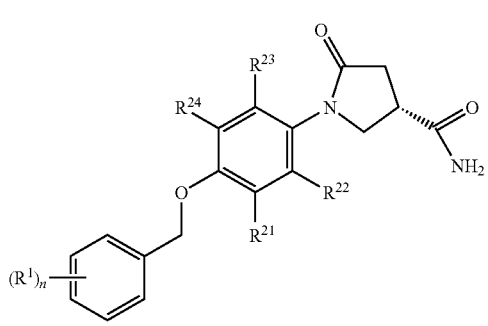

(III)

wherein
$R^1$ is halogen, halogen-$(C_1$-$C_6)$-alkyl, cyano, $(C_1$-$C_6)$-alkoxy or halogen-$(C_1$-$C_6)$-alkoxy;
$R^{21}$, $R^{22}$, $R^{23}$ and $R^{24}$ are each independently selected from the group consisting of hydrogen and halogen; and
n is 0, 1, 2 or 3.

2. The compound of claim 1, wherein:
$R^1$ is 3-fluoro;
$R^{21}$, $R^{22}$, $R^{23}$ and $R^{24}$ are each hydrogen; and
n is 1.

3. A salt of the compound of formula (S)-(II):

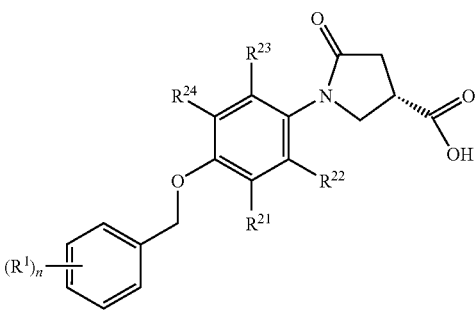

((S)-II)

with a compound selected from the group consisting of (R)-(−)-2-phenylglycinol, cinchonidine, D-phenylalaminol, (+)-phenylethylamine, (1S,2R)-(−)-cis-1-amino-2-indanol, and L-phenylephrine;
wherein
$R^1$ is halogen, halogen-$(C_1$-$C_6)$-alkyl, cyano, $(C_1$-$C_6)$-alkoxy or halogen-$(C_1$-$C_6)$-alkoxy;
$R^{21}$, $R^{22}$, $R^{23}$ and $R^{24}$ are each independently selected from the group consisting of hydrogen and halogen; and
n is 0, 1, 2 or 3.

4. The salt of claim 3, of the compound of formula (S)-(II) with (R)-(−)-2-phenylglycinol.

5. The salt of claim 3, wherein:
$R^1$ is 3-fluoro;
$R^{21}$, $R^{22}$, $R^{23}$ and $R^{24}$ are each hydrogen; and
n is 1.

6. The salt of claim 5, of the compound of formula (S)-(II) with (R)-(−)-2-phenylglycinol.

* * * * *